United States Patent [19]

Huffman

[11] Patent Number: 4,481,162

[45] Date of Patent: Nov. 6, 1984

[54] FLEXIBLE MOLD FOR DENTAL MODEL BASES AND METHOD OF USING IT

[75] Inventor: Ronald E. Huffman, Tucson, Ariz.

[73] Assignee: KV33 Corporation, Tucson, Ariz.

[21] Appl. No.: 483,833

[22] Filed: Apr. 11, 1983

Related U.S. Application Data

[63] Continuation-in-part of Ser. No. 230,330, Feb. 2, 1981, Pat. No. 4,378,929.

[51] Int. Cl.³ .................. B29C 1/02; B29C 1/14; B29C 7/00; B28B 7/06
[52] U.S. Cl. ..................... 264/334; 249/54; 249/127; 433/54; 425/DIG. 44
[58] Field of Search ................. 433/54-67; 249/54, 127; 264/334; 425/DIG. 44

[56] References Cited

U.S. PATENT DOCUMENTS

| | | | |
|---|---|---|---|
| 1,587,821 | 6/1926 | Darcissac | 433/55 |
| 2,138,254 | 11/1938 | Mink | 433/56 |
| 2,337,036 | 12/1943 | Erdle | 425/DIG. 44 |
| 2,430,525 | 11/1947 | Miller | 433/54 |
| 2,621,406 | 12/1952 | McPhee | 433/62 |
| 2,894,288 | 7/1959 | Brindis | 425/DIG. 44 |
| 3,159,914 | 12/1964 | De Pietro | 433/56 |
| 3,161,917 | 12/1964 | Wiland | 249/54 |
| 3,632,278 | 1/1972 | Hall | 425/DIG. 44 |
| 3,824,051 | 7/1974 | Van Leemput | 425/DIG. 44 |
| 3,966,165 | 6/1976 | Psensky | 425/DIG. 44 |
| 3,998,422 | 12/1976 | Putzer | 425/DIG. 44 |

FOREIGN PATENT DOCUMENTS 212241 12/1923 United Kingdom ................. 433/55

OTHER PUBLICATIONS

Leckey, "Stretchiest Rubber Yet . . . ", Popular Mechanics, vol. 129#4, Apr. 1968, pp. 117-119.

*Primary Examiner*—Willard E. Hoag
*Attorney, Agent, or Firm*—Cahill, Sutton & Thomas

[57] ABSTRACT

A flexible mold defining either a full base or a quadrant base of a dental model includes a perimeter member for defining the side walls of the base and a shelf extending inwardly from the rear side wall for delineating a slot at the rear of the base, which slot is useable for indexing an arm of an articulator to be attached to opposed ones of the bases. A variant of the mold permits the formation of a pedestal for supporting a matching tooth die. A method of removing the molded article from the mold is also disclosed and claimed.

10 Claims, 16 Drawing Figures

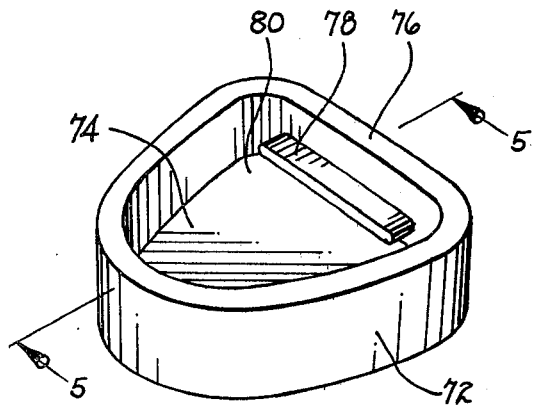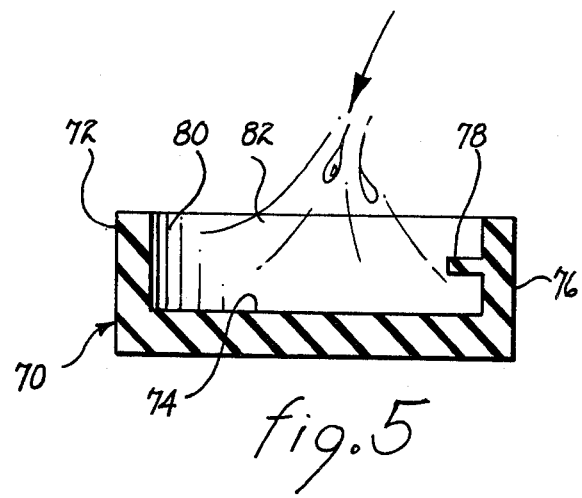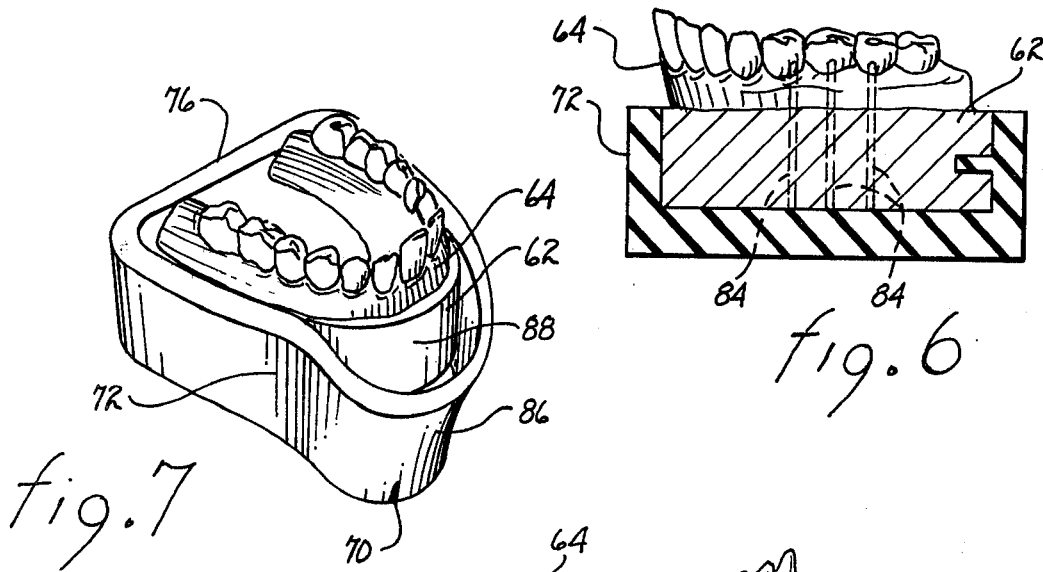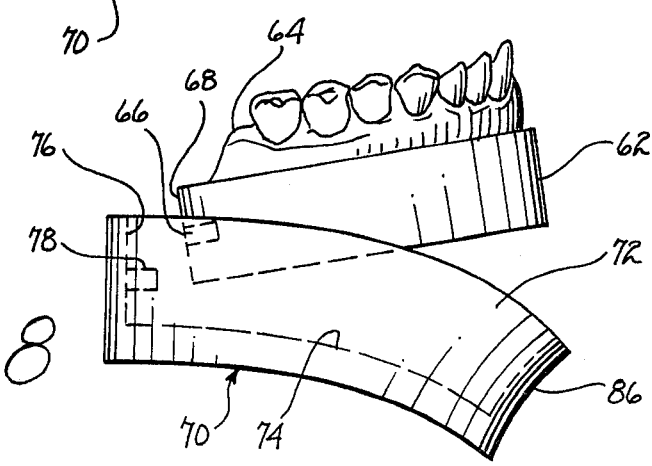

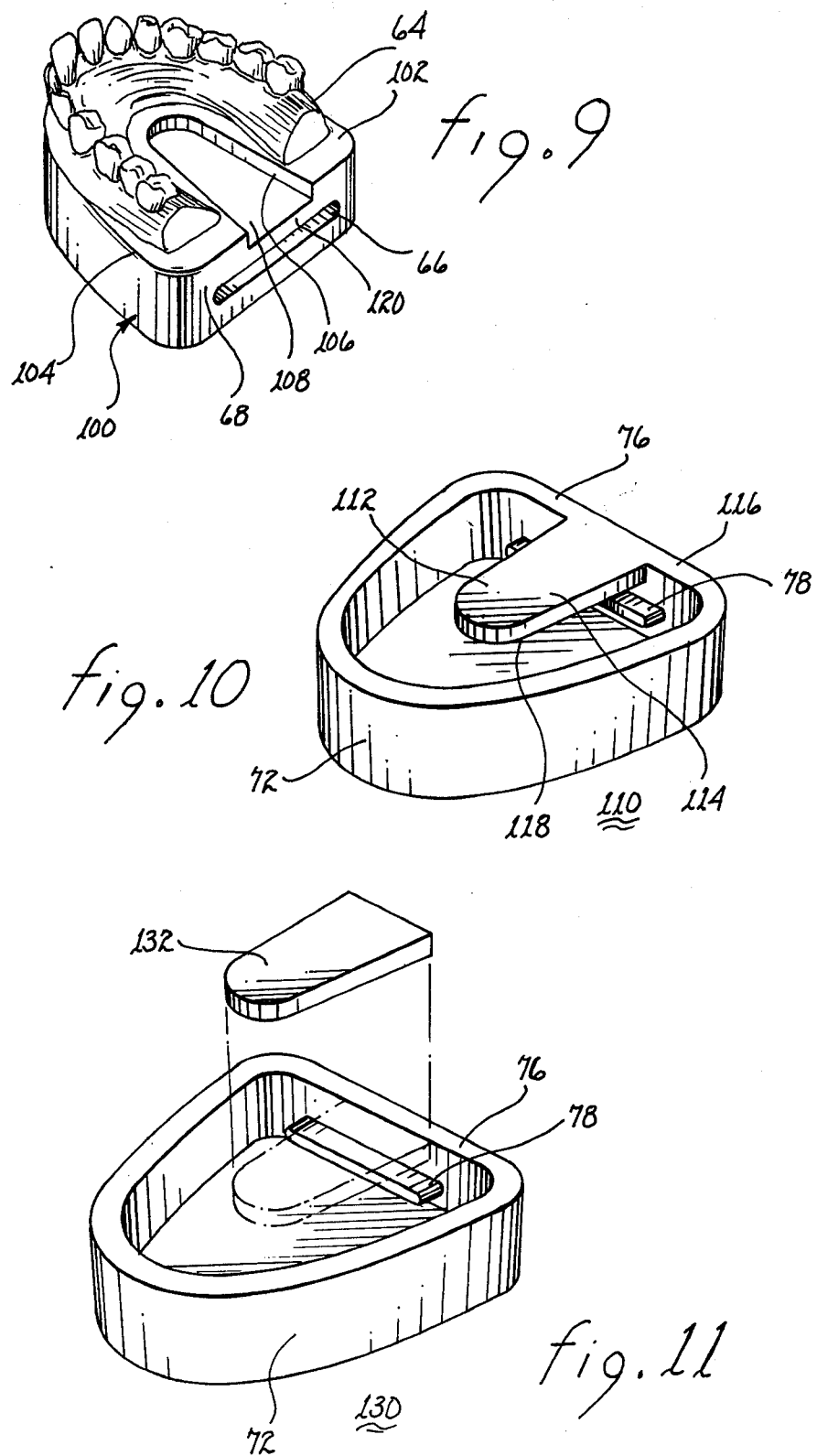

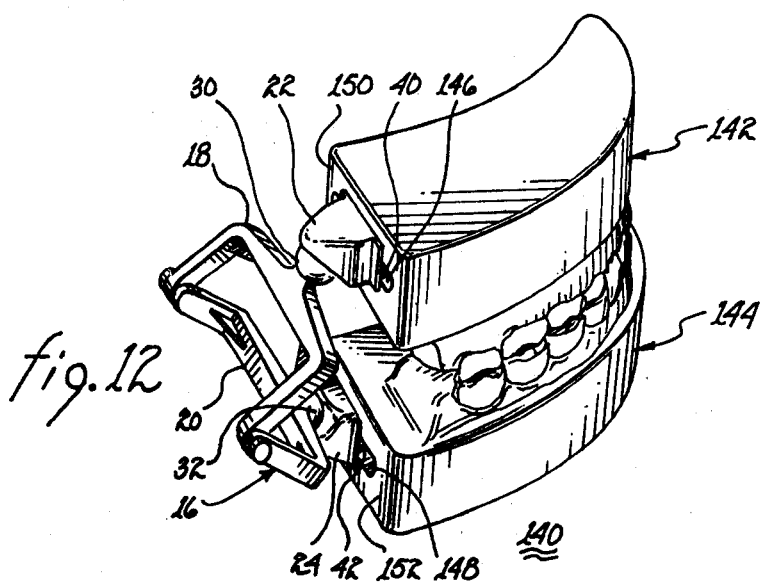
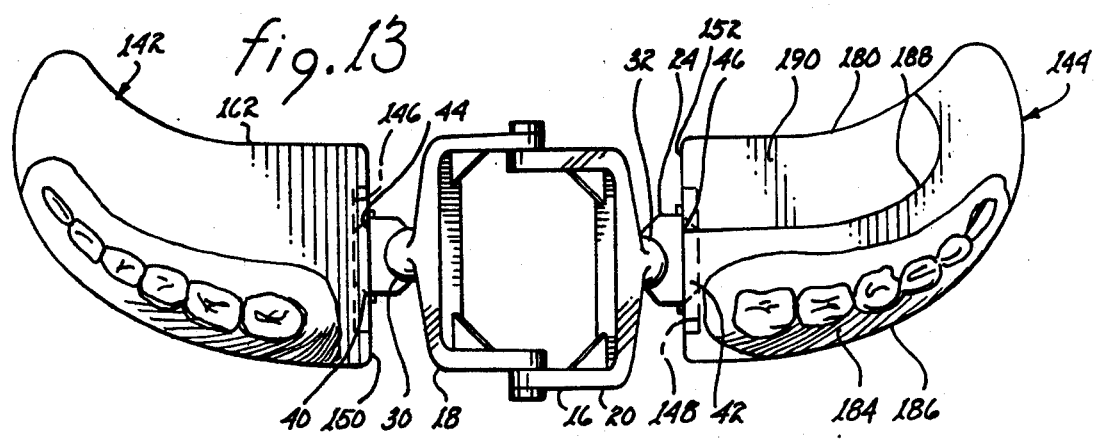
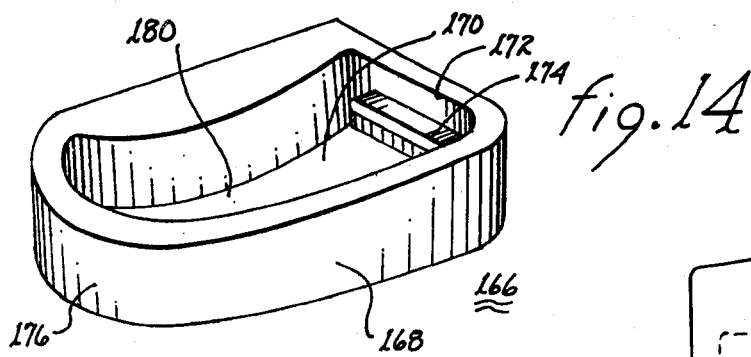
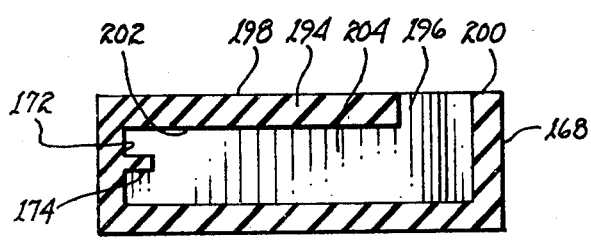
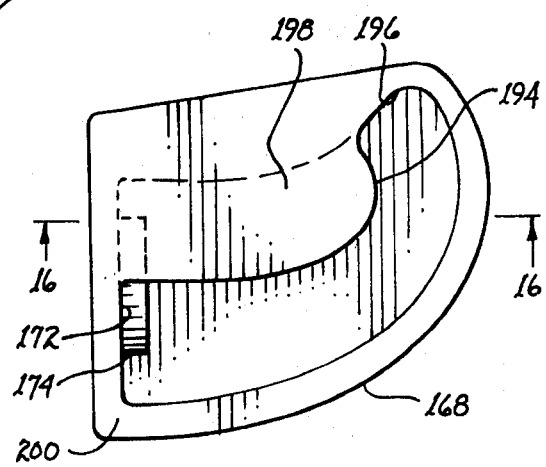

FLEXIBLE MOLD FOR DENTAL MODEL BASES AND METHOD OF USING IT

The present application is a continuation-in-part application of copending patent application Ser. No. 230,330 entitled "MOLD FOR DENTAL MODELS" filed Feb. 2, 1981 and assigned to the present assignee, now U.S. Pat. No. 4,378,929 issued Apr. 5, 1983 and is related to copending application Ser. No. 261,562 entitled "DENTAL MODEL ARTICULATOR", filed May 7, 1981, and assigned to the present assignee, now U.S. Pat. No. 4,382,787.

The present invention relates to dental models and, more particularly, to molds and methods for using same to form the base of a dental model.

To accurately form and position false teeth or caps, a dentist normally makes a negative impression of the affected tooth or teeth. The negative impression may be partial, unilateral or bilateral, depending upon the extent of work to be done; the negative impression serves as a mold for developing a die of the patient's teeth. The negative impression is obtained by partially filling a tray with thermoplastic material. The filled tray is inserted within the patient's mouth such that the teeth and adjacent gum sink into and create a cavity within thermoplastic material. Shortly thereafter, the thermoplastic material will cure and retain an exact impression of the patient's teeth and adjacent gum. This is an essentially standard technique presently used by most dentists.

To form a tooth die, a pourable casting stone, known as "pink stone" is poured into the negative impression up to at least the "margin" or base of the tooth. The pink stone is compacted to preclude voids and remove any air bubbles. After the pink stone is at least partially cured, wax or similar lubricant is swathed upon the surface of the pink stone.

In the prior art, the base for the dental mold is made by one of two methods. First, additional pourable hardenable stone, generally referred to as "yellow stone", is poured within the negative impression to cover the pink stone and the retainer with sufficient depth of yellow stone to form a solid base. After both the pink stone and the yellow stone have hardened, the tray and supported thermoplastic material is peeled away to leave a conventional dental model. Alternatively, a patty of yellow stone is formed upon a glass or other smooth surface. The partially or completely cured pink stone is placed thereupon.

In either method, pins are lodged or fixated in the pink stone to extend into and slidably engage the yellow stone. Usually, three pins per model tooth to be worked on are used. The pins serve the function of maintaining registration of the model tooth with respect to the remaining die.

Either of the prior art methods for making the base of yellow stone requires substantial technician time to manually form the yellow stone into an initial shape. After it is cured, further time is required for cutting and grinding away excess yellow stone material. The time spent and material wasted necessarily adds to the cost of the dental model to the ultimate detriment of the patient.

Either of the above processes for making the bases of dental models tends to result in each base being somewhat unique and individualized. When the dental models are placed upon a dental articulator to perform work on the dental model, a substantial amount of time and expertise is necessary to properly attach and align the upper and lower coacting dental models to reproduce the relationship of the patient's jaws. The requisite time for aligning the dental models is exacerbated by the nonuniformity of the dental model base configurations and thicknesses and requires yet further time and effort to positionally orient and attach each base upon its respective arm of the articulator.

The dental base described and illustrated in patent application Ser. No. 230,330, is formed by pouring the yellow stone into a mold. The mold standardizes the width, breath, height and configuration of the base. Such standardization permits the use of indexing means in the bases to mount opposing bases of a dental model upon an articulator. Additionally, there is described and illustrated the use of an overhang for forcing a depression in the surface of the base to which the tooth die is attached, which depression delineates a platform. The tooth die (pink stone) is attached upon the platform. To sever a model tooth from the tooth die, mesial and distal saw cuts are made through the tooth die to a point just below the line of demarcation between the tooth die and the base. The line of demarcation is coincident with the surface of the platform. As the saw blade need not be angled to have the saw end clear the opposing quadrant of the tooth die, the depth of cut into the base may be minimized at a point just below the platform surface.

In patent application Ser. No. 261,562, there is described an articulator attachable to opposed pairs of dental model bases through a mounting means. The articulator, as illustrated in the application, is particularly easily useable with size standardized bases for dental models of the type described in patent application Ser. No. 230,330. One embodiment of the mounting means useable as part of the articulator includes a tab, tang or ridge for penetrable engagement with a slot formed in the rear sidewall of a dental model base.

The present invention is directed to a uniformly sized full or quadrant dental model base having a slot formed within the rear sidewall and to a method for making such a base. Optionally, the base may include a platform for supporting the tooth die; the method and mold for forming the optional base is also described.

It is therefore a primary object of the present invention to provide a standard sized base for full or quadrant dental models.

Another object of the present invention is to provide a standard sized base for dental models and which base includes a keyway to receive a key of an arm of an articulator.

Still another object of the present invention is to provide a base for a dental model adapted to key with an articulator arm which base includes a platform for supporting the tooth die.

Yet another object of the present invention is to provide a method for making a standard sized dental model base for use with an articulator, which base requires no manual shaping or finishing to attach it to an arm of the articulator.

A further object of the present invention is to provide a method for forming a slot in the rear sidewall of a standard sized base of a dental model.

A yet further object of the present invention is to provide a flexible mold for making a standard sized base for a dental model, which base includes a slot in the rear sidewall and a raised platform to support a tooth die.

A still further object of the present invention is to provide a flexible mold for a base of a dental model which mold forms a platform for a tooth die and a slot in the rear sidewall of the base.

These and other objects of the present invention will become apparent to those skilled in the art as the description thereof proceeds.

The present invention may be described with greater specificity and clarity with reference to the following drawings, in which:

FIG. 4 illustrates a mold for making a model dental base;

FIGS. 5, 6, 7 and 8 illustrates a method for molding a standard sized dental model base;

FIG. 9 illustrates a variant of the dental model base formed in accordance with the present invention;

FIGS. 10 and 11 illustrate molds for developing the dental model base illustrated in FIG. 9;

FIG. 12 is a perspective view of a quadrant model dental base attached to an articulator;

FIG. 13 is a top view illustrating two configurations of a quadrant model dental base attached to an articulator;

FIG. 14 illustrates a mold for making a quadrant model dental base; and

FIGS. 15 and 16 illustrate a mold for making a variant of the quadrant model dental base.

In the practice of prosthetic dentistry, one very important technical problem in the shaping and fitting of the restoration occlusal surfaces to register, meet and operatively cooperate with opposed surfaces in conformity with the established habits, idiosyncrasies and tooth facet inclinations of the user. The many factors peculiar to the individual have heretofore made proper operative correlation of the restoration with the associated dental elements almost invariably a matter susceptible of satisfactory resolution only through repetitious adjustments and modifications had in the dental chair after installation of the restoration. This occurs despite the use of fixed, even though adjustable, mechanically simulated axis of articulation, planes and arcs of occlusion, lines, planes and axis of symmetry and the link which fail to provide the full orbital range necessary for reconstitution of the natural dental relationships determinable from the traces and indices upon and established through use of the original dentures. To facilitate attainment of the desired operative registration between restorations and their associated dental elements and thereby largely obviate the necessity for adjustments and corrections in the dental chair, the present invention provides dental model bases particularly configured to mate with a specifically configured articulator to provide a device for laboratory use by dentists or technicians wherein the relationship to be redintegrated can be fully and accurately portrayed and operatively duplicated as a check mounting for the restoration.

Figure 1:
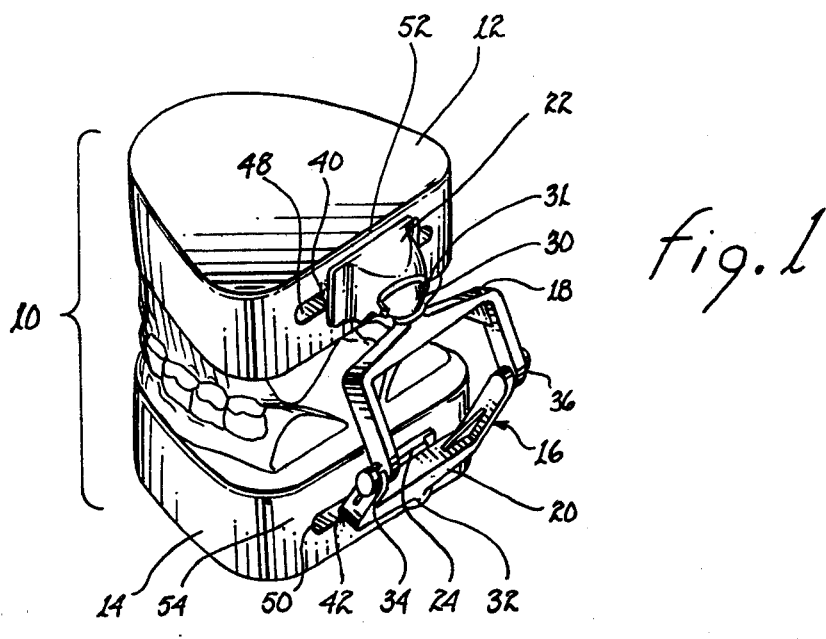
FIG. 1 is a perspective view of the present invention attached to an articulator.

Referring to FIG. 1, there is shown a complete dental model 10 having a pair of mating full dental model casts 12 and 14 simulative of the original dentures and the condition requiring restoration or correction. An articulator 16 is attached to the casts to maintain them positionally simulative of the natural relationships portrayed when substantially in parallel relationship at one limit of the range of relative movement. A pair of interconnecting elements or brackets 18 and 20 are pivotally attached to one another and are of resilient flexible material sufficient to accommodate relative movement about all axis and within all planes between the casts in simulation of the operative range and pattern of the original dentures.

Figure 2:
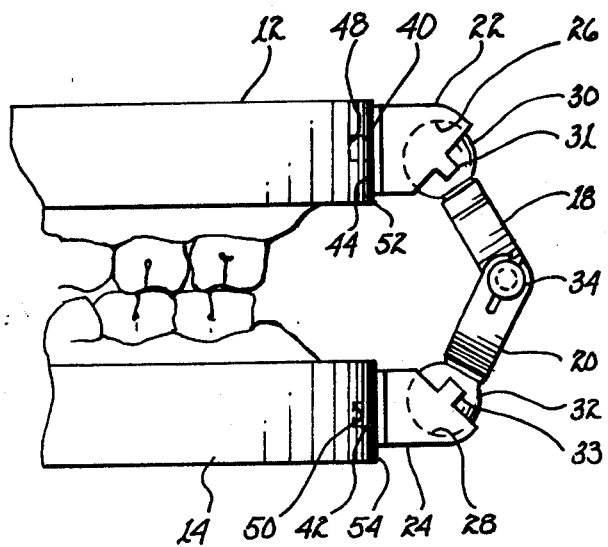
FIG. 2 is a side view showing the present invention attached to an articulator.

Referring jointly to FIGS. 1 and 2, further details of articulator 16 and its relationship to casts 12 and 14 will be described. First and second mounting means 22 and 24 are attached to casts 12 and 14, respectively. Each mounting means includes a semi-spherical or partially spherical depression disposed at the respective extremity. In example, mounting means 22 includes depression 26 and mounting means 24 includes depression 28. Brackets 18 and 20 include spheres 30, 32 sized to receivingly mate with depressions 26, 28, respectively. Brackets 18 and 20 are pivotally joined to one another by pivot means 34, 36; the pivot means may be a flexible interconnection or of the snap fit type illustrated.

To mount articulator 16, mounting means 22 and 24 are attached to the rear faces of the respective casts. Spheres 30 and 32 are located within the respective depressions 26, 28 upon angular adjustment of the respective brackets to obtain the requisite spatial relationship therebetween; nominally, the brackets define an interior obtuse angle. To maintain the casts in the predetermined fixed spatial relationship to one another at one limit of the range of relative movement, an adhesive is applied intermediate the spheres and their respective depressions to fixedly secure the respective brackets in fixed angular orientation with respect to the mounting means. Pivotal movement of the casts is effected by relative angular displacement between the joined brackets about the respective pivot means or hinge line. Translational movement in any plane and rotational movement about any axis of the casts with respect to one another is accommodated by the flexing brackets 16 and 18.

Mounting means 22 and 24 may be generally triangular in one plane to provide an apex within which the depressions (26, 28) are formed. To simplify manipulation of articulator 16 during attachment to the casts and fixation of the angular relationship between the brackets and the mounting means, retaining fingers 31 and 33 may be employed to extend from the perimeter of depressions 26, 28, respectively. These fingers are of resilient material and in the quiescent state, cant toward one another to provide snap retention for a sphere inserted within the respective depressions. By the use of such fingers, the components of articulator 16 are retained attached to one another during positioning of casts 12 and 14. Upon achievement of the initial positioning orientation of the casts, an adhesive, such as any one of the commercially available fast setting cyanoacrylate or anaerobic adhesives, may be employed to fixate each sphere within its respective depression.

Mounting means 22 and 24 include a key or ridge 40, 42 extending from planar side 44, 46 of the respective mounting means. A receptacle, keyway or slot 48, 50 is formed in rear wall 52, 54, respectively, of bases 12, 14 to matingly receive the ridge of the respective mounting means. The resulting mechanical engagement between the mounting means and the casts, in combination with mastic or adhesive disposed therebetween, rigidly secures each mounting means to its respective cast.

Preferably, each slot 48, 50 is wider than the ridge to be inserted therein to permit lateral movement in attaching the respective mounting means thereto and to permit deliberate offset attachment of the articulator for particular purposes. Mounting means 22 and 24 are preferably of plastic and formed by any one of several available plastic forming techniques; whereby, the size, positioning and angular relationship between the ridge and the respective side of the mounting means can be controlled to close tolerances. Through the method to be described below, the height, width, length and configuration of each of bases 12 and 14 can be standardized and the configuration, positioning and angular orientation of slots 48, 50 with respect to the rear walls 52, 54 of the casts can be held to close tolerances. The resulting fit achievable between each slot and its ridge along with the parallelism achievable between each slot and its ridge along with the parallelism achievable between the opposing adjacent sides and rear walls create a strong mechanical junction between each cast and the respective mounting means of the articulator. The further use of an adhesive to bond the mounting means to the casts insures maintenance of a fixed relationship therebetween.

Figure 3:
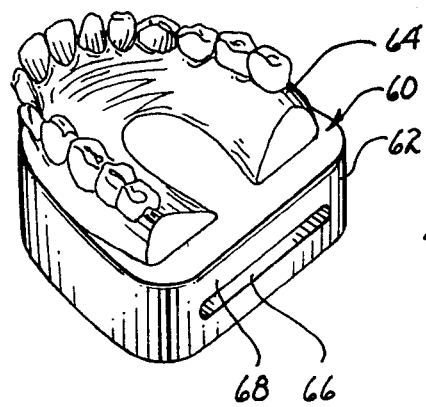
FIG. 3 is a perspective view illustrating a dental model base constructed in accordance with the present invention.

Referring to FIG. 3, there is shown a standard sized dental model cast 60 having a base 62 upon which has been mounted a model tooth die 64. A slot 66 extends horizontally inwardly from rear wall 68 as described above; this slot receives a corresponding ridge from one of the mounting means of the articulator.

Referring jointly to FIGS. 4 to 8, a mold 70 for developing base 62 will be described. Mold 70 is formed as a monolithic unit of a rubber or rubber-like compound to provide sufficient rigidity to delineate the configuration of the base to be formed and yet permit outward bending and stretching of the mold sidewalls to effect release and removal of the formed base. An example of a suitable rubber compound is sold by the Friedheim Tool Supply Company under the mark Jofre.

A continuous sidewall 72 extends upwardly from a substrate or floor 74. The junction therebetween may be sharp edged, as illustrated, or may be curved, depending upon manufacturing consideration attendant formation of the mold. Sidewall 72 includes a rear sidewall 76 for defining the planar rear wall 68 of the base to be formed (see FIG. 3). A protrusion or shelf 78, parallel with floor 74, extends inwardly into mold cavity 80. The shelf is disposed approximately midway up the surface of rear sidewall 76 and forms an indentation or slot in the base.

To form a dental model cast 60 (see FIG. 3), yellow stone 82 in a flowable state is poured into mold cavity 80. The yellow stone will flow beneath and around shelf 78 and up to a level coincident with the top of continuous sidewall 72. A screed or the like may be employed to obtain a level top surface of the yellow stone. Before the yellow stone sets, a tooth die 64 (pink stone), having a plurality of dowels or pins 84 depending therefrom is placed upon the uncured exposed surface of base 62. Preferably, the extending part of pins 84 is commensurate in length with the thickness of base 62, as shown in FIG. 6; the pins are coated with a release agent to permit sliding engagement with the base after the yellow stone is cured.

After curing of the yellow stone, front end 86 of continuous sidewall 72 is pried forwardly and downwardly away from the corresponding front 88 of base 62 to permit manual grasping of the base. Thereafter, the base is pulled forwardly of mold 70 to permit sliding disengagement between shelf 78 and the resulting slot 66 formed in base 62. These steps are particularly illustrated in FIGS. 7 and 8. Thereafter, the mold is released, which release permits it to resume its shape as depicted in FIG. 4. The mold is now ready to be used in the making of a further base 62. The dental model cast withdrawn from mold 70 corresponds to the configuration illustrated in FIG. 3. It is now ready for attachment to articulator 16.

Referring to FIG. 9 there is illustrated a variant 100 of the base. This variant incorporates a pedestal 102 upon which tooth die 64 is mounted. As described in further detail in patent application Ser. No. 230,330, pedestal 102 provides certain advantages to a dentist or laboratory technician during the steps attendant severing of a model tooth by making mesial and distal saw cuts through the tooth die to a point just below the line of demarcation between the tooth die and the base. The pedestal is defined by the peripheral edge 104 of variant 100 and edge 106 of an elongated recess or depression 108 extending forwardly from rear wall 68 of the variant.

A mold 110 for forming variant 100 is illustrated in FIG. 10. This mold is very similar to mold 70 shown in FIG. 4 and includes all elements and features thereof. In addition, an overhang 112 extends forwardly from rear sidewall 76; top surface 114 of the overhang being essentially in the same plane as top surface 116 of continuous sidewall 72. Bottom surface 118 of the overhang is vertically upwardly displaced from shelf 78 to provide a certain amount of physical strength to segment 120 (see FIG. 9) of the base and segregating depression 108 from slot 66.

The method for forming variant 100 is mold 110 and removing it therefrom is duplicative to the method described above with respect to FIGS. 5 through 8.

Referring to FIG. 11, there is illustrated a further mold 130, which mold is a variant of mold 110. Herein, the overhang is a tongue 132 segregated from rear sidewall 76.

During the making of a base like variant 100 with mold 130, the yellow stone is poured into the mold. On completion of the step of pouring, tongue 132 is imbedded in the top surface of the flowable yellow stone in abutting relationship with rear sidewall 76, as shown in phantom lines in FIG. 11. After during of the yellow stone, the tongue is manually pried out of the yellow stone. Thereafter, mold 130 is removed from the solidified base formed of the yellow stone in the manner depicted in FIGS. 7 and 8.

The primarily benefit of the use of tongue 132 rather than an attached overhang 112 is related to the removal of variant 100 formed. Depending upon various factors, such as the effectiveness of a release agent, if employed, the smoothness of inner surfaces of the mold forming the mold cavity and the flexibility of the mold, greater or lesser difficulty may be encountered in segregating both shelf 78 and overhang 112 from the base after curing of the yellow stone. Such difficulties are obviated by the removability of tongue 132 prior segregation of the mold itself from about the cast.

It may be pointed out that the variant of base 62 depicted in FIG. 9 is formable by either of molds 110 and 130. Mold 130 has the further advantage that it may be employed to form base 62 (see FIG. 3) as well simply by not embedding tongue 132 in the yellow stone.

Referring to FIG. 12, there is shown a complete dental model 140 having a pair of mating quadrant dental model casts 142, 144 simulative of the original dentures and the condition requiring restoration or correction. An articulator 16, like that shown and described with respect to FIGS. 1 and 2, is attached to the casts to maintain them positionally simulative of the natural relationships portrayed when substantially in parallel relationship at one limit of the range of relative movement. Mounting means 22, 24 include a ridge 40, 42, respectively, extending from planar side 44, 46 of the respective mounting means. A slot 146, 148 is formed in rear wall 150, 152, respectively, of bases 154, 156 of casts 142, 144 to matingly receive the ridge of the respective mounting means. The resulting mechanical engagement between the mounting means and the casts, in combination with mastic or adhesive disposed therebetween, rigidly secures each mounting means to its respective cast.

Referring to FIG. 13, there is shown a standard sized quadrant dental model cast 142 having a base 162 upon which has been mounted a model tooth die 164. Slot 146 extends horizontally inwardly from rear wall 150. As described above, this slot receives a corresponding ridge from one of the mounting means of the articulator.

A mold 166 for developing base 162 will be described with reference to FIG. 14. The mold is formed as a monolithic unit of rubber or rubber-like compound to provide sufficient rigidity to delineate the configuration of the base to be formed and yet permit outward bending and stretching of the mold sidewalls to effect release and removal of the formed base. A continuous sidewall 168 extends upwardly from substrate or floor 170. The sidewall includes a rear sidewall 172 for defining the planar rear wall 150 of the base (see FIG. 13). A shelf 174, parallel with floor 170, extends inwardly into mold cavity 174. The shelf is disposed approximately midway up the surface of rear sidewall 172.

To form a quadrant dental cast 142 (see FIG. 13), yellow stone in a flowable state is poured into mold cavity 180. The yellow stone will flow beneath and around shelf 174 and up to a level coincident with the top of continuous sidewall 168. A screed or the like may be employed to obtain a level to surface of the yellow stone. Before the yellow stone sets, a tooth die 164 having a plurality of pins depending therefrom is placed upon the uncured exposed surface of the base. Preferably, the extending part of the pins is commensurate in length with the thickness of the base.

After the yellow stone has cured, front end 176 of continuous sidewall 168 is pried forwardly and downwardly away from the corresponding front of the base formed to permit grasping of the base. Thereafter, the base is pulled forwardly of mold 166 to permit sliding disengagement between shelf 174 and the resulting slot 146 formed in base 162. Reference may be made to FIGS. 7 and 8 for these steps.

Referring to FIG. 13 there is illustrated a variant 180 of quadrant base 162. The variant incorporates a pedestal 182 upon which die 184 is mounted. The pedestal is defined by peripheral edge 186 of variant 180 and edge 188 of an elongated depression 190 extending forwardly along one side from rear wall 152 of the variant.

A mold 192 for forming variant 180 is illustrated in FIGS. 15 and 16. This mold is similar to mold 166 illustrated in FIG. 14 and includes all features and elements thereof. In addition, overhang 194 extends forwardly from rear sidewall 172 and along lateral side 196. Top surface 198 of the overhang is essentially in the same plane as top surface 200 of continuous sidewall 168. Bottom surface 202 of the overhang is vertically upwardly displaced from shelf 174 to provide a certain amount of physical strength to the segment of yellow stone between slot 148 and the surface of depression 190.

The method for forming variant 180 within mold cavity 204 and removing it therefrom is duplicative of the method described with respect to mold 166.

In the event difficulty in removing the variant arises due to the overhang or if such removal tends to foreshorten the life of the mold, the overhang may be made removable in the manner of tongue 132 illustrated in FIG. 11. Such configuration permits the use of a single mold such as modl 166 to be employed to make either base 162 or variant 180. It is to be understood that mirror image molds are required for left and right quadrants.

While the principles of the invention have now been made clear in an illustrative embodiment, there will be immediately obvious to those skilled in the art many modifications of structure, arrangement, proportions, elements, materials and components, used in the practice of the invention which are particularly adapted for specific environments and operating requirements without departing from those principles.

I claim:

1. In a method for forming from a pourable hardenable compound deposited therein the base of a dental model useable with an articulator, the improvement comprising the steps of:
    (a) defining the perimeter of a mold cavity and the opening to the mold cavity, which opening is essentially dimensionally coincident with the maximum dimensional planform of the mold cavity with a flexible sidewall and an upper edge of the sidewall, respectively;
    (b) further defining the bottom of the mold cavity with a flexible substrate cooperating with cavity with a flexible substrate cooperating with the sidewall to define the bottom and lateral surfaces of the mold cavity;
    (c) forming with a protrusion attached to a limited portion of the sidewall and extending within the perimeter of the mold cavity along a projection axis and partially across the mold cavity a receptacle within the base to which receptacle the articulator may be attached;
    (d) removing the base formed from the mold cavity by bending the sidewall and substrate in concert to lower that part of the upper edge of the sidewall across the mold cavity from the location of the protrusion; and
    (e) withdrawing the formed based from the mold cavity substantially along the projection axis of the protrusion to allow sliding disengagement of the protrusion from within the receptacle formed in the base.

2. The method as set forth in claim 1 wherein said step of forming includes the step of forming the indentation at a location intermediate the upper edge of the sidewall and the substrate.

3. In a method for forming from a pourable hardenable compound deposited therein the base of a dental model useable with an articulator, the improvement comprising the steps of:
    (a) defining the perimeter of a mold cavity and a planform essentially dimensionally coincident with the maximum dimensional planform of the mold cavity with a flexible sidewall and an upper inner edge of the sidewall, respectively;

(b) further defining the bottom of the mold cavity with a flexible substrate cooperating with the sidewall to define the bottom and lateral surfaces of the mold cavity;

(c) forming a receptacle within the base to which receptacle the articulator may be attached with a shelf attached to a limited portion of the sidewall and extending within the perimeter of the mold cavity along a projection axis and partially across the mold cavity;

(d) further forming with an overhang projecting from a further limited portion of the sidewall and extending within the perimeter of the mold cavity and only partially across the mold cavity a depression within the base and delineating a platform on the base upon which platform a tooth die of the dental model may be supported;

(e) removing the formed base from the mold cavity by bending the sidewall and substrate in concert to lower the part of the upper edge of the sidewall across the mold cavity from the location of the protrusion; and (f) withdrawing the formed base from the mold cavity substantially along the projection axis of the protrusion to allow sliding disengagement of the protrusion from within the receptacle formed in the base.

4. A flexible mold for forming from a pourable hardenable compound deposited therein the base of a dental model useable with an articulator, said mold comprising in combination:

(a) a flexible sidewall for defining the perimeter of a mold cavity generally triangular in planform and having an upper edge for defining the opening to the mold cavity, which opening is essentially dimensionally coincident with the maximum dimensional planform of the mold cavity;

(b) a flexible substrate for defining a generally flat bottom of the mold cavity, said substrate and said sidewall member cooperating to define the bottom and lateral surfaces of the mold cavity;

(c) a shelf attached to a limited portion of said sidewall and extending within the perimeter of the mold cavity along a projection axis substantially parallel to the bottom and only partially across the mold cavity for delineating a receptacle within the base to which receptacle the articulator may be attached; and (d) said substrate and said sidewall being bendable in concert to lower sufficiently that part of said upper edge of said sidewall across the mold cavity from the location of said shelf to permit withdrawal of the formed base from the mold cavity along the projection axis of said shelf and allow sliding disengagement of said shelf from which the receptacle formed in the base.

5. The mold as set forth in claim 4 wherein said limited sidewall portion corresponds to the base portion of the triangular planform.

6. A flexible mold for forming from a pourable hardenable compound deposited therein the base of a dental model useable with an articulator, said mold comprising in combination:

(a) a flexible sidewall for defining the perimeter of a mold cavity generally triangular in planform and having an upper inner edge for defining a planform essentially dimensionally coincident with the maximum dimensional planform of the mold cavity;

(b) a flexible substrate for defining a substantially flat bottom of the mold cavity, said substrate and said sidewall member cooperating to define bottom and lateral surfaces of the mold cavity;

(c) a shelf attached to a limited portion of said sidewall and extending within the perimeter of the mold cavity along a projection axis and only partially across the mold cavity for delineating a receptacle within the base to which receptacle the articulator may be attached;

(d) an overhang projecting from a further limited portion of said sidewall and extending within the perimeter of the mold cavity and only partially across said mold cavity for forming a depression within the base and for delineating a platform on the base upon which platform a tooth die of the dental model may be supported; and (e) said substrate and said sidewall being bendable in concert to lower sufficiently that part of said upper edge of said sidewall across the mold cavity from the location of said shelf to permit withdrawal of the formed base from the model cavity along the projection axis of said shelf and allow sliding disengagement of said shelf from within the receptacle formed in the base.

7. The mold as set forth in claim 6 wherein said overhang extends into the mold cavity below the plane defined by said upper edge of said sidewall.

8. The mold as set forth in claim 6 wherein said limited portion and said further limited portion are at least partially vertically overlapping to locate said shelf vertically between said substrate and said overhang.

9. The mold as set forth in claim 6 wherein said sidewall defines the mold cavity as generally triangular in planform having a base and two sides extending from opposed ends of the base to an apex.

10. The mold as set forth in claim 6 wherein said overhang is detached from said sidewall.

* * * * *